United States Patent
Skierski et al.

(10) Patent No.: US 7,042,566 B2
(45) Date of Patent: May 9, 2006

(54) METHOD OF VERIFYING COLOR AND STRENGTH PROPERTIES OF BATCHES OF WOOD STAINS

(75) Inventors: Thomas J. Skierski, Brunswick Hills, OH (US); Thomas L. Cope, Lyndhurst, OH (US)

(73) Assignee: The Sherwin-Williams Company, Cleveland, OH (US)

(*) Notice: Subject to any disclaimer, the term of this patent is extended or adjusted under 35 U.S.C. 154(b) by 0 days.

(21) Appl. No.: 10/811,094

(22) Filed: Mar. 26, 2004

(65) Prior Publication Data

US 2004/0223149 A1 Nov. 11, 2004

Related U.S. Application Data

(60) Provisional application No. 60/458,320, filed on Mar. 27, 2003.

(51) Int. Cl.
*G01J 3/42* (2006.01)

(52) U.S. Cl. .................................. 356/319; 356/408

(58) Field of Classification Search ............... 356/408, 356/421, 425, 319, 300, 402; 427/256
See application file for complete search history.

(56) References Cited

U.S. PATENT DOCUMENTS

| | | | |
|---|---|---|---|
| 3,368,864 A | 2/1968 | Gugerll | 8/25 |
| 3,690,771 A | 9/1972 | Armstrong, Jr. et al. | 356/176 |
| 4,887,217 A | 12/1989 | Sherman et al. | 364/468 |
| 5,116,408 A * | 5/1992 | Crozer | 524/388 |
| 5,231,472 A | 7/1993 | Marcus et al. | 356/402 |
| 6,166,814 A | 12/2000 | Pringle | 356/445 |
| 6,362,885 B1 | 3/2002 | Osumi et al. | 356/402 |
| 6,719,452 B1 * | 4/2004 | Schermacher et al. | 366/132 |

OTHER PUBLICATIONS

S. Upton Jenkins, Consultant to Hunter Associates Laboratory, Inc., Reston, VA, "*Batch Color Correction by Trisitimulus Colorimeter*", Modern Paint and Coatings, Sep. 1980, pp. 41-44 Marshall M. Lib., Catholic University of America, "*Color Technology*", Chemical Engineering, Aug. 12, 1968, pp. 146-156.

* cited by examiner

*Primary Examiner*—Layla G. Lauchman
(74) *Attorney, Agent, or Firm*—Vivien Y. Tsang; Robert E. McDonald; Paul R. Katterle

(57) ABSTRACT

A method of verifying the color and tinting strength of a manufactured batch of a semi-transparent wood stain. In accordance with the method, a standard batch of the wood stain is formed and then mixed with a specified amount of a white colorant to form a standard measurement batch. A test sample of the manufactured batch is obtained and is also mixed with a specified amount of the white colorant to form a test measurement sample. Layers of the standard measurement batch and the test measurement sample are formed on the substrates and complete hide obtained. Reflectance measurements of the layers are made using a spectrophotometer. The reflectance measurements are used to determine if the color and the tinting strength of the manufactured batch is within an acceptable deviation range of the color and tinting strength of the standard batch. This allows for objective color difference and tint strength difference calculations, and adjustments can be made therefrom, therefore eliminating the past visual trial and error methods.

6 Claims, 1 Drawing Sheet

METHOD OF VERIFYING COLOR AND STRENGTH PROPERTIES OF BATCHES OF WOOD STAINS

CROSS-REFERENCE TO RELATED APPLICATION

This application claims the benefit of U.S. Provisional Application No. 60/458,320, filed Mar. 27, 2003.

BACKGROUND OF THE INVENTION

The present invention relates to semi-transparent wood stains and, more specifically, to a method of objectively verifying properties of batches of semi-transparent wood stains.

Stains are semitransparent solutions or suspensions of coloring matter (such as dyes or pigments or both) in a vehicle, designed to color a surface by penetration without hiding it or leaving a continuous film. In contrast, paints are opaque solutions or suspensions of coloring matter in a vehicle, designed to hide or cover a surface with an opaque film.

Stains are typically manufactured in batches pursuant to a formula that specifies specific amounts of binder, colorants and other ingredients. Due to differences in the properties of ingredients from one batch to another and irregularities in processing, the color and tinting strength of a manufactured batch of a particular stain may vary from the standard color and tinting strength for the stain. Conventionally, quality control of the color of a manufactured batch of a stain is conducted by a colorist who takes a sample of the manufactured batch and applies it to a wood sample and then visually compares the stained wood sample to a piece of wood treated with the stain having the standard color and strength. If the visual inspection indicates that the color of the manufactured batch does not match the standard color of the stain, the colorist subjectively determines what changes need to be made to the manufactured batch and then the changes are made. A sample of the modified manufactured batch is then applied to the wood sample and another comparison is made. These steps are repeated until the colorist determines that the color of the manufactured batch matches the standard color of the stain. The same steps are followed to adjust the strength. As can be appreciated, such a trial-and-error method is tedious and relies upon the skill of the colorist for its effectiveness. Moreover, visual inspection typically cannot discern differences between the tinting strength of the manufactured batch and the standard tinting strength of the stain. As a result, manufactured batches could potentially be produced having unnecessarily high tinting strengths, which is uneconomical. Accordingly, there is a need in the art for an improved method of verifying and, if necessary, changing the color and tinting strength of batches of wood stains. The present invention is directed to such a method.

SUMMARY OF THE INVENTION

This invention is directed to a method of verifying at least one property of a manufactured batch of a semi-transparent wood stain that is produced using a selected formula, said method comprising the steps of providing a spectrophotometer; forming a standard batch of the wood stain using the selected formula; adding a first set amount of a white colorant to the standard batch to form a standard measurement batch; forming a standard layer of the standard measurement batch on a first substrate such that the standard layer completely hides the first substrate; obtaining a test sample of the manufactured batch; adding a second set amount of the white colorant to the test sample to form a test measurement sample, wherein the proportion of the second set amount of the white colorant to the test sample is substantially the same as the proportion of the first amount of the white colorant to the standard batch; forming a test layer of the test measurement sample on a second substrate such that the test layer completely hides the second substrate; obtaining reflectance measurements of the standard layer and the test layer using the spectrophotometer; and using the reflectance measurements to determine if the at least one property of the manufactured batch is within an acceptable deviation range of at least one property of the standard batch. The method of this invention can verify color differences and tinting strength of wood stains.

BRIEF DESCRIPTION OF THE DRAWINGS

The features, aspects, and advantages of the present invention will become better understood with regard to the following description, appended claims, and accompanying drawings where:

DETAILED DESCRIPTION OF THE INVENTION

Figure 1:
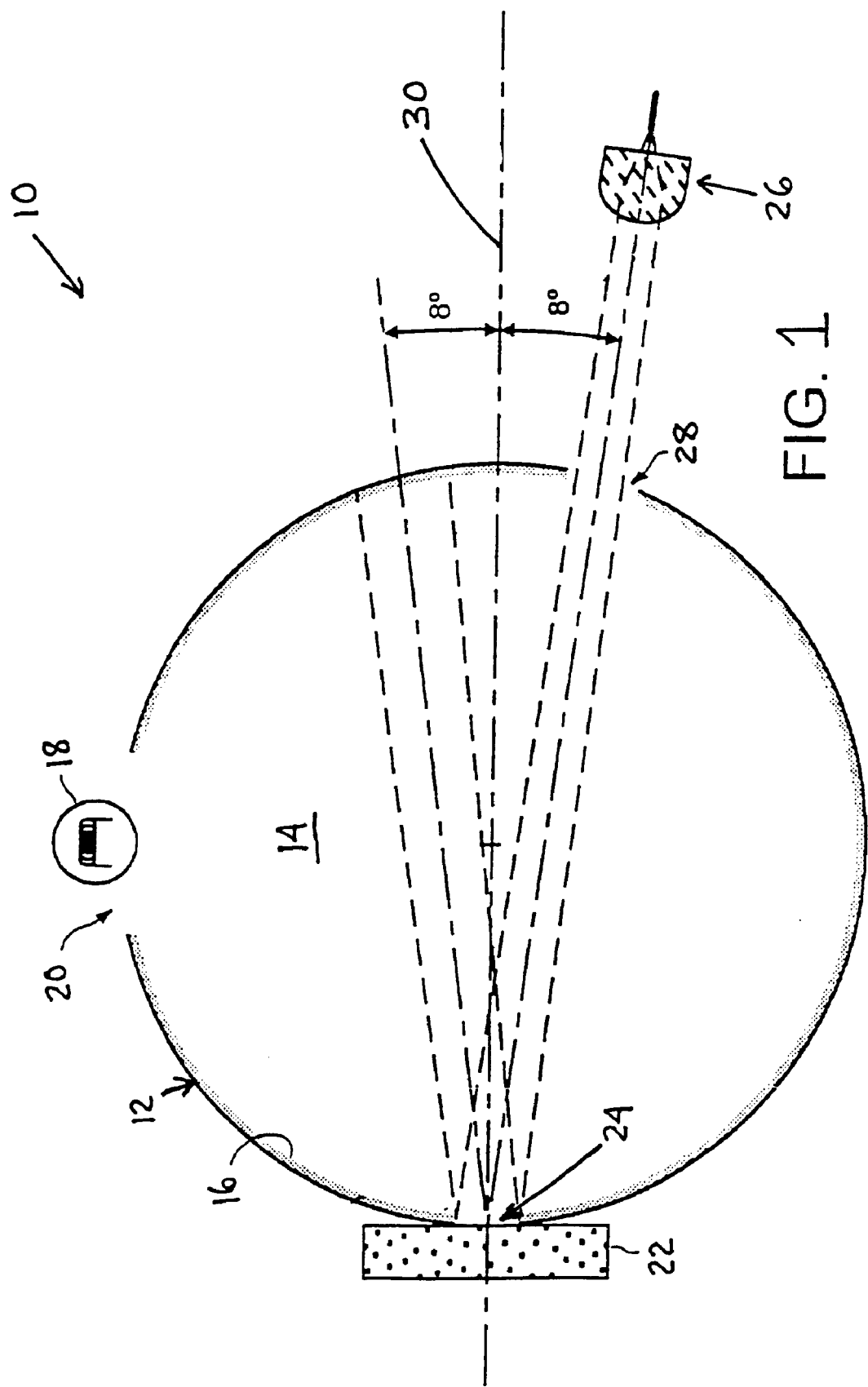
FIG. 1 is a schematic view of a portion of a single angle spectrophotometer for use in the method of the present invention.

As used herein, the term "wood stain" shall mean a semitransparent solution or suspension of coloring matter (such as dyes or pigments or both) in a vehicle (binder and thinner), designed to color a piece of wood by penetration without hiding it or leaving a continuous film. Wood stains typically have low solids contents relative to paint, i.e., less than 20 percent by weight solids.

Wood stains can be oil-based or water-based. Oil-based wood stains generally comprise one or more pigments, a binder such as an alkyd resin containing a drier, and organic solvents such as mineral spirits, VMP naphtha, kerosene, xylene, toluene or a mixture of these. In contrast, water-based wood stains have waterborne binders such as acrylic emulsions and water dilutable alkyds.

As used herein, the term "vehicle" shall mean a binder and one or more thinners and optionally other ingredients (excluding colorants) used to form wood stains.

As used herein, "colorant" shall mean a substance that imparts color to another material or mixture. Colorants can be either dyes or pigments (organic or inorganic). Pigments are insoluble in the vehicle, whereas dyes are soluble in the vehicle. Inorganic pigments include metal oxides such as the oxides of iron, titanium, zinc, cobalt, and chrome. Earth pigments may utilize mineral pigments obtained from clay. Various forms of carbon may be used for black pigments. Organic pigments are insoluble in the vehicle and are derived from natural or synthetic materials, and include phthalocyanine, lithos, toluidine, and para red. Organic pigments may be employed in a precipitated form as a lake. Dyes are organic materials and include acid dyes, such as azo, diazo and triarylmethane dyes, and basic dyes, such as aniline dyes.

Pigment-based colorants are often provided in the form of tinting concentrates comprising highly concentrated levels of color pigment dispersed into a vehicle. The amount of color pigment used in a colorant is typically from about 5 weight percent to about 70 weight percent, depending on the type of color pigment.

As used herein the term "chromatic colorant" shall mean a colorant that is not black, white or grey.

As used herein, the term "tinting strength" shall mean the measure of the effectiveness with which a unit quantity of wood stain alters the color of a wood substrate. The concentration of colorants in a wood stain contributes to tinting strength in a major way.

One of the components of the present invention relates to the measurement of color. Briefly, color is a sensation evoked by the physical stimulation of color photoreceptor cone cells in the human retina. The stimulation consists of electromagnetic radiation in the visible spectrum comprising wavelengths between 380 and 700 nm. The photoreceptor cone cells can be separated into three classes, with each class being sensitive to a different spectral distribution of radiation. This trichromacy of color sensation permits the color of an object to be described by three numerical components, such as the tristimulus values X, Y and Z, which are based on the tristimulus responses x, y, and z of a standard observer that were developed through experimentation by the Commission Internationale de L'Éclairage (CIE) in 1931. More specifically, the tristimulus values X, Y and Z are the integrals of the products of the functions x, y and z with the radiant energy distribution functions from the object. The tristimulus value X is the red primary, the tristimulas value Y (which is equal to the luminous reflectance or transmittance) is the green primary, and the tristimulus value Z is the blue primary.

The total color difference between two objects is referred to as $\Delta E$ and is generally calculated as the square root of the sum of the squares of chromaticity difference $\Delta C$, and the lightness difference, $\Delta L$: $\Delta E=[(\Delta C)^2+\Delta L^2]^{1/2}$. Color difference equations are well known in the art and are used to transform the tristimulus values X, Y and Z into a more uniform matrix that can be used to calculate $\Delta E$.

The spectral characteristics of an object can be determined from reflectance measurements taken by a spectrophotometer using the Kubelka-Munk Theory. As is well known, the Kubelka-Munk Theory relates reflectance at complete hiding (R) of a paint film at a specific wavelength to two optical constants, K (the absorption coefficient) and S (the scattering coefficient). After some basic assumptions, the Kubelka-Munk Theory can be expressed by the following equation:

$$\frac{K}{S} = \frac{(1-R)^2}{2R}$$

The present invention is directed to a method of verifying the color and tinting strength properties of a manufactured batch of wood stain. More specifically, the present invention is directed to a method of measuring the color and tinting strength of a manufactured batch of wood stain, comparing these measurements to the standard color and tinting strength for the wood stain, and, if necessary, changing the color and/or tinting strength of the manufactured batch of the wood stain. The method of the present invention may be used for both oil-based and water-based wood stains.

The method utilizes a single angle spectrophotometer 10 connected to a personal computer with a central processing unit. The computer may run a color matching software program that is proprietary to the assignee of the present invention, namely The Sherwin-Williams Company. The color matching software program may include a plurality of databases containing spectral data for colorants applied to substrates in the manner described below. The color matching software program may also contain one or more formula(s) for wood stain composition(s) (ex colorants) describing the required proportions of vehicle and other additives.

As shown in FIG. 1, the spectrophotometer 10 may have an integrating sphere 12 defining a cavity 14 with a highly reflective, optically diffuse surface 16. A light source 18 connected to the cavity 14 via a lamp port 20 illuminates the cavity 14 to diffusely illuminate a specimen 22 at a specimen port 24. A receiver 26 is positioned at a receiver port 28 to receive optical radiation from the specimen 22. The receiver 26 may be positioned normal to the specimen 22, along the diameter of the sphere 12, or, more preferably, at angle of up to 10°, more preferably about 8° from the specimen normal 30. The receiver 26 conveys the reflected light from the specimen 22 to a light analyzer (not shown). The light analyzer also receives reference light from the light source, which is used to correct for variations in the intensity of the light source. The light analyzer includes a device for separating light into its component wavelengths, such as a diffraction grading or a prism, and an array of detectors to measure the intensities of the different wavelengths. Signals from the detector array are multiplexed and fed to a data processor (not shown), which produces digital signals that are conveyed to the personal computer.

A commercially-available single angle spectrophotometer that may be used in the present invention is the ColorEye 7000 color spectrophotometer sold by Gretag Macbeth.

In a first part of the method of the present invention, standard measurement batches are produced for wood stains that are to be manufactured in a production facility. A white colorant is used to form the "standard" measurement batch and should be the same type of white colorant that is specified for the wood stain system to be manufactured. If no white colorant is available in that particular system, one must be developed (procedure under separate explanation). Preferably, the white colorant is added in an amount sufficient to provide the standard measurement batch with a Y value of about 70, as determined by the spectrophotometer. Typically, about 100 parts of the white colorant are used per 20 parts of the standard batch of the wood stain. The amount of the white colorant added to the standard batch is recorded and the same white colorant will be used to form a "test sample" of the manufactured batch of the wood stain.

If the tints for a particular wood stain system does not specify a white colorant, a standard is carefully prepared by omitting one of the chromatic colorants of the tints from the wood stain formula, and substituting it with titanium dioxide.

Once the standard measurement batches are produced using a compatible white colorant, they are carefully applied to Leneta hide charts in even coats to provide complete hiding. Typically, the thickness of the coats on the hide charts is about 6 mils. After the coats of the standard test measurement batches are dry, reflectance readings of the coats may be taken using the spectrophotometer 10. Each reading comprises a plurality of reflectance measurements made at 10 to 20 nanometer intervals along the visible light spectrum. Using these reflectance measurements, the X, Y and Z tristimulus values for each of the standard measurement batches may be calculated according to the formulas:

$$X = \sum_{\lambda} ER_x$$

$$Y = \sum_{\lambda} ER_y$$

$$Z = \sum_{\lambda} ER_z$$

where E is the relative energy of a standard light source, R is the reflectance of the standard measurement batch and x, y, z are the color functions for a specified observer. The X, Y and Z tristimulus values may be stored in the personal computer for later use.

After a manufactured batch of a wood stain has been produced in the production facility, a test sample of the manufactured batch is taken for measurement. An equal portion, or substantially the same amount, of the identified test white colorant as used for the standard measurement batch above is added to the test sample of the manufactured batch. As set forth above, the ratio of white:standard sample or white:test batch sample is typically 100/20. The test measurement is carefully applied to a Leneta hide chart in an even coat to provide complete hiding. The thickness of the coat is typically about 6 mils. After the coat of the test measurement sample is dry, a reflectance reading of the coat is taken using a spectrophotometer. The reading comprises a plurality of reflectance measurements made at 10 to 20 nanometer intervals along the visible light spectrum. Using the formulas described above for the standard measurement batches, the X, Y and Z tristimulus values for the test measurement sample are calculated, and thereby ΔE values can be calculated.

Although it is preferred that the standard measurement for all of the wood stain colors manufactured at a production facility be prepared and their reflectance measurements taken and stored in the personal computer before any manufacturing batches of the wood stains are produced, the present invention is not limited to this sequence of steps. The standard measurement batch color for a particular wood stain may be prepared and its reflectance reading taken at the same time or even after the test measurement sample for a manufactured batch of the wood stain color is prepared and its reflectance reading taken.

Using the reflectance readings of the standard measurement batch and the test measurement sample, the color and tinting strength of the manufactured batch is compared to the color and tinting strength of the standard batch of the wood stain. More specifically with regard to color, a software program associated with the spectrophotometer 10 or loaded on the personal computer uses the reflectance readings to calculate the color difference (ΔE) between the standard measurement batch and the test measurement sample. If the calculated ΔE is within an acceptable deviation range, the color of the manufactured batch is deemed to be acceptable. If the calculated ΔE is outside the acceptable deviation range, a colorist views the tristimulus values X, Y, and Z of the standard measurement batch and the test measurement sample and subjectively determines the additional amount(s) of one or more of the colorants (used in the formula for the wood stain) that need to be added to the manufactured batch to move the color of the manufactured batch toward the color of the standard batch so as to produce a ΔE that is within the acceptable deviation range. The additional amount(s) of colorant(s) is/are then added to the manufactured batch. A new test measurement sample may then be produced and coated on a hide chart and additional reflectance readings taken for comparison to the standard measurement batch. This process may be repeated until the ΔE is within the acceptable deviation range.

Although the colorist must still subjectively determine the additional amount(s) of colorant(s) that need to be added in the event the ΔE is outside the acceptable deviation range, the colorist is provided with objective tristimulus values X, Y, and Z, which greatly help the colorist make his/her determination and is a vast improvement over simply visually viewing a stained piece of wood, where the color is affected by the wood substrate, the opacity, and the viewer.

Instead of subjectively determining the amount(s) of colorant(s) that need(s) to be added, it is contemplated that a color matching software program loaded on the personal computer may be used to determine the amount(s) of colorant(s) that need(s) to be added. The color matching software program would include a plurality of databases containing spectral data (K and S values) for colorants applied to Leneta hide charts in a manner similar to that described above for the standard measurement batches and the test measurement sample.

With regard to the tinting strengths of the standard measurement batch and the test measurement sample for the manufactured batch, the K/S value of the standard measurement batch at the wavelength with the lowest reflectance (maximum absorption) is compared to the K/S value of the test measurement sample at the same wavelength. If the difference between the two K/S values is within an acceptable deviation range, the tinting strength of the manufactured batch is deemed to be acceptable. If the difference between the two K/S values is outside the acceptable deviation range, additional proportional amounts of the colorants may be added if the difference indicates that the tinting strength of the manufactured batch is too weak, or additional vehicle may be added if the difference indicates that the tinting strength of the manufactured batch is too strong.

The tinting strength of the manufactured batch may be expressed as a percentage of the tinting strength of the standard batch, where the percentage is calculated using the ratio of the K/S value of the test measurement sample to the K/S value of the standard measurement batch.

The method of the present invention provides a number of benefits. The method permits different batches of a particular wood stain to be manufactured with consistent properties of color and tinting strength and enables a manufacturer to provide an end user customer with objective evidence of this consistency, namely ΔE's and tinting strength percentages. The ability to provide different batches of the wood stain with consistent tinting strengths prevents batches of wood stain from being manufactured with tinting strengths that are too weak and, thus not of acceptable quality, or too strong, which wastes colorants, wastes product itself, and is uneconomical.

While the invention has been shown and described with respect to particular embodiments thereof, those embodiments are for the purpose of illustration rather than limitation, and other variations and modifications of the specific embodiments herein described will be apparent to those skilled in the art, all within the intended spirit and scope of the invention. Accordingly, the invention is not to be limited in scope and effect to the specific embodiments herein described, nor in any other way that is inconsistent with the extent to which the progress in the art has been advanced by the invention.

What is claimed is:

1. A method of verifying at least one property of a manufactured batch of a semi-transparent wood stain that is produced using a selected formula, said method comprising the steps of:
   providing a spectrophotometer;
   forming a standard batch of the wood stain using the selected formula;
   adding a first set amount of a white colorant to the standard batch to form a standard measurement batch;
   forming a standard layer of the standard measurement batch on a first substrate such that the standard layer completely hides the first substrate;
   obtaining a test sample of the manufactured batch;
   adding a second set amount of the white colorant to the test sample to form a test measurement sample, wherein the proportion of the second set amount of the white colorant to the test sample is substantially the same as the proportion of the first amount of the white colorant to the standard batch;
   forming a test layer of the test measurement sample on a second substrate such that the test layer completely hides the second substrate;
   obtaining reflectance measurements of the standard layer and the test layer using the spectrophotometer; and
   using the reflectance measurements to determine if the at least one property of the manufactured batch is within an acceptable deviation range of at least one property of the standard batch.

2. The method of claim 1, wherein the at least one property of the manufactured batch of the semi-transparent wood stain is color.

3. The method of claim 1, wherein the at least one property of the manufactured batch of the semi-transparent wood stain is tinting strength.

4. A method of verifying at least one property of a manufactured batch of a semi-transparent wood stain that is produced using a selected formula, said method comprising the steps of:
   providing a spectrophotometer;
   forming a standard batch of the wood stain using the selected formula;
   adding a first set amount of a colorant to the standard batch to form a standard measurement batch;
   forming a standard layer of the standard measurement batch on a first substrate such that the standard layer completely hides the first substrate;
   obtaining a test sample of the manufactured batch;
   adding a second set amount of the colorant to the test sample to form a test measurement sample, wherein the proportion of the second set amount of the colorant to the test sample is substantially the same as the proportion of the first amount of the colorant to the standard batch;
   forming a test layer of the test measurement sample on a second substrate such that the test layer completely hides the second substrate;
   obtaining reflectance measurements of the standard layer and the test layer using the spectrophotometer; and
   using the reflectance measurements to determine if the at least one property of the manufactured batch is within an acceptable deviation range of at least one property of the standard batch.

5. The method of claim 4, wherein the at least one property of the manufactured batch of the semi-transparent wood stain is color.

6. The method of claim 4, wherein the at least one property of the manufactured batch of the semi-transparent wood stain is tinting strength.

* * * * *